(12) United States Patent
Jankoski et al.

(10) Patent No.: US 6,202,465 B1
(45) Date of Patent: *Mar. 20, 2001

(54) METHOD FOR FORMING ENDOSCOPIC INSTRUMENT BODY

(75) Inventors: Frank Jankoski, Phillipsburg; Harry Lehn, Somerville, both of NJ (US)

(73) Assignee: Micro Stamping Corporation, Somerset, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/264,212

(22) Filed: Mar. 5, 1999

(51) Int. Cl.[7] .................................................. B21D 51/16
(52) U.S. Cl. ........................................... 72/368; 72/379.2
(58) Field of Search .............................. 72/51, 368, 404, 72/339, 379.2

(56) References Cited

U.S. PATENT DOCUMENTS

| | | |
|---|---|---|
| 1,793,352 | 2/1931 | Bell . |
| 2,004,555 * | 6/1935 | Kleinmann et al. .................... 72/404 |
| 3,245,242 | 4/1966 | Maier . |
| 3,299,493 | 1/1967 | Gehrt . |
| 3,440,852 * | 4/1969 | Heath ..................................... 72/368 |
| 3,566,660 * | 3/1971 | Dedek .................................... 72/339 |
| 3,691,601 | 9/1972 | Hough . |
| 4,266,310 | 5/1981 | Perrault . |
| 4,495,551 * | 1/1985 | Foltz .................................... 72/379.2 |
| 5,862,579 | 1/1999 | Blumberg . |

FOREIGN PATENT DOCUMENTS

| | | |
|---|---|---|
| 4223247 | 1/1994 | (DE) . |
| 0154236 | 6/1988 | (JP) . |

* cited by examiner

*Primary Examiner*—Lowell A. Larson
(74) *Attorney, Agent, or Firm*—Stroock & Stroock & Lavan LLP

(57) ABSTRACT

A method for forming a metal tube includes providing a flat sheet of metal, forming features in the sheet, forming a strip within the sheet, the features being disposed within the strip, progressively forming the strip into a barrel, and trimming the barrel from the sheet.

11 Claims, 3 Drawing Sheets

METHOD FOR FORMING ENDOSCOPIC INSTRUMENT BODY

BACKGROUND OF THE INVENTION

This invention is directed to method of forming an endoscopic instrument body from metal, in particular, a method for forming an endoscopic instrument body by rolling the metal.

Endoscopic instruments generally have an outer sheet and an endoscopic instrument body contained within the sheet and a bundle within the endoscopic instrument body. The bundle may comprise anything from cables for controlling a tool at a distal end of the endoscopic instrument body to light fibers and electrical wires for supporting a light and camera at the end of the endoscopic instrument body. The tube supports the bundle as it is inserted into a patient. The endoscopic instrument bodies are formed of metal to provide support and protection to the bundle as it is used during an operation. To that end the endoscopic instrument bodies are formed of metal such as stainless steel because of their strength and rigidity across a distance.

In order to support the bundles within the endoscopic instrument body, to make them functional, the sides of the endoscopic instrument body are often cut, provided with openings, slits, or other features (collectively referred to as features) so that the bundle within the endoscopic instrument can interact with other parts of the endoscope not within the endoscopic instrument body. The jobs to be performed by the endoscopic instrument will determine the bundle and the type of bundle will determine the types of features placed on the endoscopic instrument body.

It is known from the prior art to form seamless tubes, a plug of metal is drawn to a predetermined length substantially corresponding to the length of the desired endoscopic instrument body. The inner diameter and outer diameter of the endoscopic instrument body are determined by the length of the draw. Because a predetermined amount of material is used as a starting material, the longer the tube is drawn, the thinner the endoscopic instrument body walls become changing the dimensions of the outer diameter and inner diameter. Once the endoscopic instrument body has been drawn, it is then hand finished and cut to provide the necessary features. The forming of the features within the endoscopic instrument body is usually done by hand and therefore is time consuming.

It is also known to form an, endoscopic instrument body by rolling a flat stock of metal into a tube. The tube is usually extremely long, having a length, by way of example, of 500 feet or more. The flat stock is rolled along the grain so that the tube can support a finished product having a length of 500 feet or more. The tube is rolled into a circle. Therefore the dimensions of the narrow rolled stock are the outside diameter of the roll by over 500 feet in length. The seam is then welded. A plug is inserted at one end of the tube and the tube is drawn to reduce the outer diameter of the tube until it reaches the desired outer diameter of the final endoscopic instrument body product. The 500 foot long tube is then cut to the desired endoscopic instrument body length. Once it has been cut, the features are then again added by hand.

These prior art methods have been satisfactory. However, they suffer from the disadvantage that first, because a drawing step is required in both methods of manufacture, it is difficult to produce a predetermined outer diameter and inner diameter with accuracy. Furthermore, because each process requires that the features be added after formation of the endoscopic instrument body, the features must be added by hand tooling which results in less precision, less accuracy and is time consuming.

Accordingly, a method for forming an endoscopic instrument body which overcomes the prior art shortcomings by providing a method which forms an endoscopic instrument body with greater accuracy and more efficiency is desired.

SUMMARY OF THE INVENTION

A method for forming an endoscopic instrument body is provided in which a raw flat strip stock is fed into the opening of a progressive tooling machine. In a first step, the features are formed into the flat strip stock at the appropriate positions. The flat strip is then incrementally progressively formed into a tube. The tube is then cut away from the strip completing the endoscopic instrument body.

In an exemplary embodiment, the tube is molded across the grain of the metal. In another embodiment, pilot holes are formed in the strip to orient the strip for the feature forming and progressive molding steps.

Accordingly, it is an object of the present invention to provide an improved method for forming an endoscopic instrument body.

A further object of the invention is to provide an endoscopic instrument body in which features can be formed in the endoscopic instrument body in an efficient time saving manner.

Still other objects and advantages of the invention will in part be obvious and will in part be apparent from the specification and drawings.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENT

Figure 1:
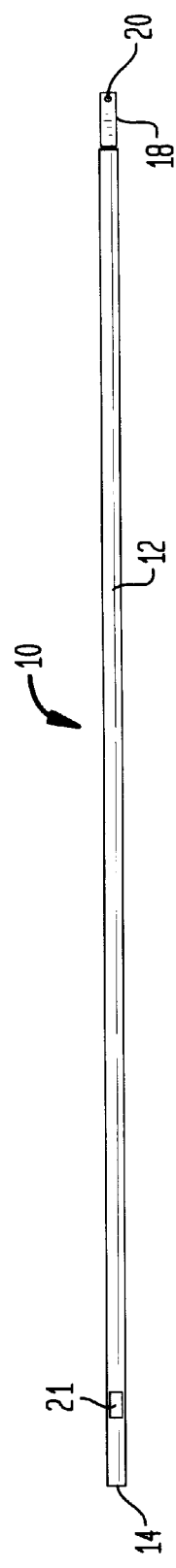
FIG. 1 is a side elevational view of an endoscopic instrument body constructed in accordance with the invention.
Figure 2:
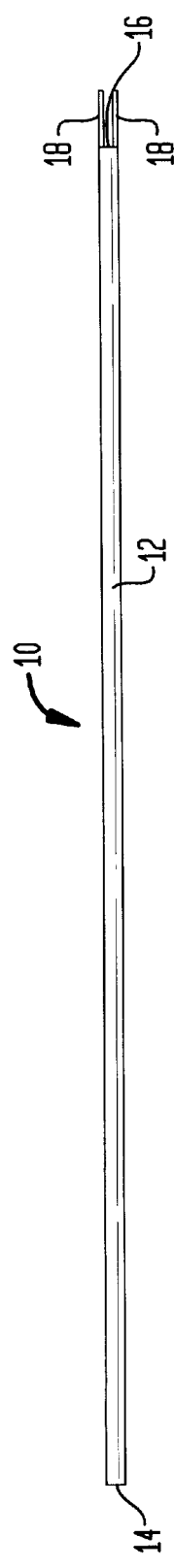
FIG. 2 is a top plan view of an endoscopic instrument body constructed in accordance with the invention.

Reference is first made to FIGS. 1 and 2 in which an endoscopic instrument body, generally indicated as 10, constructed in accordance with the present invention is provided. Endoscopic instrument body 10 has a barrel section 12 which is hollow and has an open end 14 and an open end 16 at opposed ends of barrel 12. Cuts, openings, slits, grooves, extensions and the like openly (collectively referred to as features) are provided on endoscopic instrument body 10. By way of example, a hole 21 may be provided on one or both sides of barrel 12 to provide access to barrel 12 or to provide a passage way entirely through the width of barrel 12. Referring to FIG. 2, a second type of feature may be fingers 18 provided adjacent open end 16 of barrel 12. Fingers 18 extend from barrel 12 and may be formed, for example, thinner than the thickness of the walls of barrel 12 and may also be provided with a hole 20 formed therein for connection to either the bundle (not shown) or some other operating part of the endoscopic instrument body.

Figure 3:
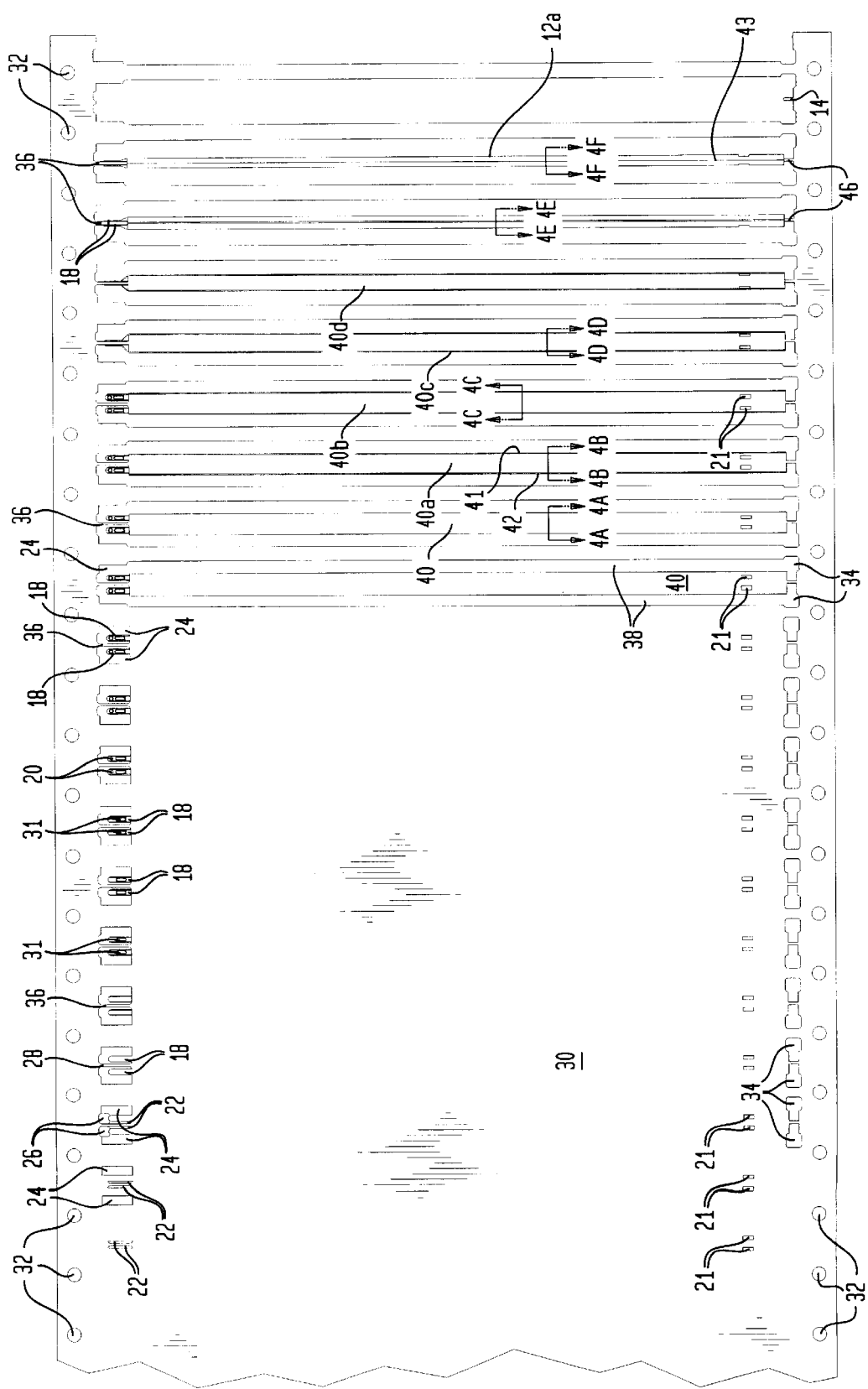
FIG. 3 is a top plan view showing a flat stock strip that has experienced different steps of the process in accordance with the invention.

Reference is now made to FIG. 3 in which a flat stock generally indicated as 30 and formed as a strip, is provided. Flat stock 30 has a substantially rectangular shape and is formed of a suitable metal such as stainless steel, by way of example. While any thickness of stock 30 may be used, preferably the stock thickness ranges from 20 to 25 thousandths of an inch. Pilot holes 32 are formed in flat stock 30 to facilitate the proper location of flat stock 30 while flat stock 30 is being fed through a machine or tool capable of performing the process to be described below. Furthermore, pilot holes 32 orient the strips relative to the machine or tool and index the strip so that the appropriate process is performed at the appropriate time in sequence.

FIG. 3 and FIGS. 4A–4G show the process for forming the endoscopic instrument body. First, pilot holes 32 are formed in a strip of flat stock 30, for example, by stamping. Then holes 21 are formed adjacent one edge of stock 30 by punching or stamping, by way of non-limiting example. Next holes 34 are either punched or stamped, for example, into sheet 30 between holes 21 and pilot holes 32. Openings 34, pilot holes 32 and holes 21 can also be cut. In a preferred embodiment, holes 34 are stamped.

At the same time, at the opposed edge of sheet 30, holes 22 are formed in sheet 30 substantially on a line with holes 21. Holes 24 are then formed either by punching, stamping, cutting or the like on both sides of holes 22. The edge of holes 24 closest to holes 21 are a distance from a leading edge of holes 34 substantially equal to the length of the endoscopic instrument body to be formed. Openings 26 are then punched to connect openings 24 and holes 22 to form fingers 18. As is shown in FIG. 3, fingers 18 are disposed within holes 24 on either side of a metal strip 36. Fingers 18 can then be further machined to add features to the fingers, such as punching openings 31 and openings 20 into fingers 18 as desired.

Holes 38 extending from holes 34 to holes 24 are then formed in strip 30. Again, holes 38 may be formed by stamping, punching or even cutting and the like. Holes 34 are separated from each other by a strip of metal carrier strip 46. Once holes 38 are punched, a strip 40 extending substantially from hole 24 to hole 34 remains. Strip 40 includes fingers 18 extending therefrom and has holes 21 formed therein. Strip 40 is affixed to strip 30 by carrier strips 36 and 46. Additionally, strip 40 extends a length equivalent to the desired length of the end product endoscopic instrument body.

Figure 4A:
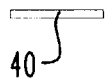
FIGS. 4A–4G are end views taken along respective sectional lines 4A–4A through 4F–4F depicted in FIG. 3 of the endoscopic instrument body as formed in accordance with the steps of the present invention.
Figure 4B:
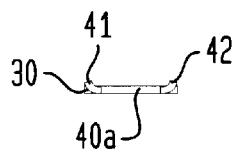
Figure 4C:
Figure 4D:
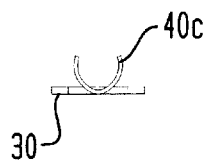
Figure 4E:
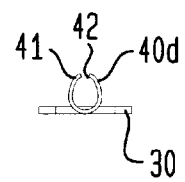
Figure 4F:
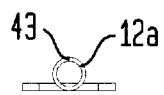
Figure 4G:
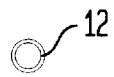

Strip 40 is then progressively formed into barrel 12 as is shown in top plan view in FIG. 3 and the corresponding side elevational views in FIGS. 4A–4F. As shown in FIG. 4A, strip 40 is originally in a flat condition. As progressive steps are performed, a first form 40*a*, having sides 41 and 42, is formed in which the edges of strip 40 are pushed upward or downward by a die (not shown) into the form shown in FIG. 4B. The die continues to curve strip 40 upward or downward into the form shown in FIG. 4C. In effect, the strip 40 is formed into what is known as the first form 40*a* in FIG. 4B, which is then again curled to form a strip 40*b* depicted in FIG. 4C. The strip is curled again to form strip 40*c* shown in FIG. 4D, and again to form precurl strip 40*d* as is shown in FIG. 4E. At this stage, edge 41 of strip 40*d* does not contact edge 42. Strip 40*d* is curled in a final curl step by pressing curl 40*d* between two form stations (not shown) to form barrel 12*a*. In this step, edges 41 and 42 meet, and, due to the pressure exerted by the form stations (which maybe on the order of 100 tons), establish a seam 43 shown in FIG. 4F. The barrel is formed in one last step as is shown in FIG. 4G by a die (not shown) to ensure that the barrel is sized correctly. Referring to FIG. 3, carrier strips 46 and 36 are then cut releasing the formed barrel 12 (depicted in FIG. 4G) from stock 30. The tube 10 is then fed down a chute to a finished components bin, completing the manufacture of endoscopic instrument body 10.

In a preferred embodiment, the grain of the metal of strip 30 extends across the strip 30 in a direction substantially perpendicular to the length of endoscopic instrument body 10. Furthermore, as discussed above, the formation of tube 12 can be accomplished through a molding process using dies known in the art for progressively bending metal.

By providing a process for forming an endoscopic instrument body utilizing progressive rolling of a stamped strip, the length and outer and inner diameters of the endoscopic instrument body are more finely controlled because the outer diameter of the endoscopic instrument body and inner diameter of the endoscopic instrument body are controlled by the thickness and width of the stamped strip, not the drawn length of the beginning metal stock. It is easier to control stamped widths and thicknesses than drawn lengths and thicknesses.

To describe the invention, an endoscopic instrument body was used by way of example. However, the novel process is applicable to the formation of any part which requires the exact formation of a barrel and in particular, a barrel which may include features to be provided therein.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting way.

It also to be understood that the following claims are intended to cover all the generic and specific features of the invention herein described and all statements of the scope of the invention which, as a matter of language might be said to fall therebetween.

What is claimed is:

1. A method for forming an endoscopic instrument body comprising:

provinding a flat sheet of metal;

forming pilot holes in the sheet at opposed first and second edges of the sheet, for orienting the sheet;

forming a strip within the sheet, said strip having at least one finger extending from said strip toward said first edge of said sheet, said at least one finger terminating in a free end spaced from said first edge;

progressively forming the strip into a barrel, the strip remaining affixed to the sheet at all times during forming by carrier strips connecting said strip and said opposed edges, said carrier strips being separate and distinct from said at least one finger; and trimming the barrel from the sheet by cutting the carrier strips.

2. The method of claim 1, further comprising:

forming features in the sheet, said features including openings.

3. The method of claim 1, wherein said features are formed by one of punching, stamping or cutting.

4. The method of claim 1, wherein said strip is formed by forming a first pair of openings along an edge of said sheet; forming a second pair of openings in the sheet, the first pair of openings and second pair of openings being separated by a first distance substantially corresponding to the length of said barrel; forming a third pair of openings; a first opening of the third pair of openings connecting a first opening of said first pair openings to a first opening of said second pair of openings, and a second of said third pair of openings connecting a second of said first pair of openings and a second opening of said second pair of openings, said first opening of said third pair of openings and said second opening of said third pair of openings being separated by a second distance, said second distance corresponding to a width of said strip.

5. The method of claim 1, wherein said sheet is disposed so that the grain of the metal extends across a width of the sheet.

6. The method of claim 5, wherein said grain of said flat sheet of metal extends substantially perpendicular to the length of the barrel.

7. The method of claim 1, wherein at least one finger hole is defined in said at least one finger.

8. The method of claim 1, wherein said at least one finger has a first thickness, said barrel having a second thickness, said first thickness being less than said second thickness.

9. A method for forming an endoscopic instrument body comprising:

providing a flat sheet of metal having first and second opposed edges;

forming a strip within the sheet, said strip having at least one finger extending from said strip toward said first opposed edge of said sheet, said at least one finger terminating in a free end spaced from said first edge;

progressively forming the strip into a barrel with the strip being affixed to the sheet, at all times during forming, by carrier strips connecting said strip and said opposed edges of the sheet, said carrier strips being separate and distinct from said at least one finger; and trimming the barrel from the sheet by cutting the carrier strips.

10. The method of claim 9, wherein at least one finger hole is defined in said at least one finger.

11. The method of claim 9, wherein said at least one finger has a first thickness, said barrel having a second thickness, said first thickness being less than said second thickness.

* * * * *